United States Patent [19]

Bockowski et al.

[11] Patent Number: 5,171,454
[45] Date of Patent: Dec. 15, 1992

[54] METHODS FOR INHIBITING THE PRODUCTION OF ACID IN ACID MINE WATERS

[75] Inventors: Edmund J. Bockowski, Furlong, Pa.; Cato R. McDaniel, The Woodlands, Tex.; Dwight P. Davis, Holland, Pa.; Patric L. Friend, Conroe, Tex.

[73] Assignee: Betz Laboratories, Inc., Trevose, Pa.

[21] Appl. No.: 746,830

[22] Filed: Aug. 19, 1991

[51] Int. Cl.⁵ .............................................. C02F 1/50
[52] U.S. Cl. .................................................. 210/764
[58] Field of Search .............................. 210/749–752, 210/758, 764–766, 919

[56] References Cited

U.S. PATENT DOCUMENTS

| | | | |
|---|---|---|---|
| 2,959,476 | 11/1960 | Overbeek | 71/2.7 |
| 3,250,667 | 5/1966 | Legator | 162/190 |
| 3,298,906 | 1/1967 | Knowles | 167/22 |
| 3,380,462 | 12/1966 | Schieber et al. | 137/3 |
| 3,690,857 | 9/1972 | Blair | 71/66 |
| 3,876,532 | 4/1975 | Dulin et al. | 210/751 |
| 4,479,820 | 10/1984 | Merk et al. | 71/67 |
| 4,724,143 | 2/1988 | Mahn et al. | 424/82 |
| 4,851,583 | 7/1989 | Bockowski et al. | 568/465 |
| 4,929,365 | 5/1990 | Clark et al. | 210/764 |
| 4,999,286 | 3/1991 | Gawel et al. | 436/518 |
| 5,000,918 | 3/1991 | Mebes | 210/764 |

OTHER PUBLICATIONS

PCT International No. WO88/04671, Jun. 1988.
"Chesapeake Corp. Finds Acrolein Biocide An Effective Economical Chlorine Substitute", Howell, WEston–Webb, *Paper Trade Journal*, 160:40–43 (1975).
"Double Duty Slimicide", Walko & Smiht, *Power Engineering*, 63:40–41 (1969).
"Control of Acid Mine Draingage by Application of Bactericidal Matrials", Erickson, Keleinmann & Onysko, Information Circular 9027, U.S. Dept. Interior (1985).

*Primary Examiner*—Thomas Wyse
*Attorney, Agent, or Firm*—Alexander D. Ricci; Philip H. Von Neida

[57] ABSTRACT

Methods are provided for inhibiting the production of acid in acid mine waters by controlling the growth of *Thiobacillus ferrooxidans* in the mine waters by adding an effective amount of acrolein. This will reduce acid mine drainage to other aqueous systems. The methods comprise adding from about 0.1 to about 10 parts acrolein per million parts of the mine water for which acid production inhibition is sought.

15 Claims, No Drawings

METHODS FOR INHIBITING THE PRODUCTION OF ACID IN ACID MINE WATERS

FIELD OF THE INVENTION

The present invention pertains to methods for inhibiting the production of acid in acid mine waters. These methods employ acrolein to control the acid-producing bacteria *Thiobacillus ferrooxidans* and related strains present in the mine.

BACKGROUND OF THE INVENTION

The production of sulfuric acid in mines and its entry into natural water sources create an ecological and economic problem. This "acid mine drainage" can have devastating effects on any water source that it enters.

During active mining operations, acid mine drainage can be controlled with some difficulty by programs utilizing neutralizing hydroxides. This treatment, however, is not easily applied after the mine site is no longer operational as acid mine drainage from former mining areas, coal refuse areas, waste-rock dumps and tailings becomes a serious problem. As the pH of a given waterway drops below 6, sensitive biota are affected. At a pH below 4, the stream will be virtually devoid of life. Further, mine acid will readily attack coexisting sulfide species and cause rapid dissolution of these minerals and release toxic concentrations of heavy metals.

Mine acid is formed under appropriate conditions by the oxidation of base metal sulfides. Microorganisms play an important role in catalyzing the oxidation of ferrous iron. The genus Thiobacillus is capable of oxidizing sulfide, thiosulfate, or elemental sulfur to sulfate and is further capable of oxidizing ferrous iron to ferric iron. Optimal pH levels for such oxidations are below 5 and generally in the area of 2.5.

When one refers to iron-oxidizing bacteria or sulfur-oxidizing bacteria, one is describing the mode of energy generation for the organisms, i.e., by oxidation of reduced iron or sulfur compounds. These types of bacteria obtain their carbon for cell growth and reproduction from $CO_2$. Thus the organisms are called chemolithotrophs, or, simply, autotrophs. *Thiobacillus ferrooxidans* is active in the pH range from about 2.0 to about 5.0, and is responsible for the production of significant amounts of sulfuric acid from mine tailings and waste rock dumps.

The conditions of an out of production mine provide all the requirements for the growth and reproduction of *Thiobacillus ferrooxidans*. These requirements include sources of sulfur compounds, ferrous ion, carbon dioxide, oxygen, and a low pH ($< 5$) water supply. The organism will thrive in this environment by growing in the crevices and niches found in the walls of the mine. An inadequate supply of gases will limit the bacteria's growth in standing mine water and in refuse piles. Seepage water trickling down the walls of the mine will not prevent growth as it does not form a barrier thick enough to inhibit gas exchange.

Many efforts have been made in order to abate the acid mine drainage problem. These included attempts at sealing mines and using reducing atmospheres, which all failed for a variety of reasons. For these reasons there is great interest in finding a method to reduce acid production in mines.

Acrolein is a known pesticide that is used to treat liquids containing slime-forming microorganisms. Acrolein has been found to effectively control bacteria, such as *Bacillus subtilis*, *Pseudomonas putrefaciens* and *Escherichia coli*; fungi such as *Penicillium italicum*, *Saccharomyces cereviseae* and *Helminthosporium turcicum*; algae; macroinvertebrates, such as snails and clams; and aquatic plants and weeds. Acrolein is also more effective than other biocides, such as chlorine, in controlling macroinvertebrates and submerged, as well as floating, aquatic weeds and algae.

From an environmental point of view, acrolein is a good biocide because it is effective, detoxified readily and inexpensively, and is non-persistent. Water solutions of acrolein are readily and conveniently neutralized for disposal with sodium bisulfite. This reaction produces a non-toxic water-soluble salt. Acrolein is also neutralized by reacting with materials present in natural waters and is therefore self-neutralizing.

Acrolein has advantages over chlorine, a common biocide used in many aqueous systems. Unlike chlorine, acrolein is less reactive with oxidizable materials or other chemical constituents usually found in both surface and well water supplies. Chlorination alone is often uneconomical for pest control in systems using waters with high chlorine demands, or in systems heavily contaminated by process leakage. In addition, chlorine is frequently not very effective against filamentous algae, bacteria and/or shellfish in heavily contaminated systems.

Thus, acrolein possesses an effective ability to kill *Thiobacillus ferrooxidans* and not merely inhibit the bacteria's growth. Its vapor pressure is of the nature that will allow it to enter the crevices and niches in a mine in the gas phase. Further, in the gas phase acrolein is effective at low concentrations. This, along with the fact that it is detoxified readily and easily neutralized, made acrolein an ideal compound to investigate for controlling mine acid production and drainage.

SUMMARY OF THE INVENTION

The present invention pertains to methods for controlling the growth of *Thiobacillus ferrooxidans* in mines comprising adding an effective amount for the purpose of acrolein to the acid mine waters.

This control of the bacteria, *Thiobacillus ferrooxidans*, will inhibit the production of sulfuric acid in the mine water and in turn will lessen the amount of acid mine drainage.

DESCRIPTION OF THE RELATED ART

U.S. Pat. No. 2,959,476, Overbeek, November 1960 discloses a method of controlling aquatic life in aqueous systems. This method is directed particularly to aquatic weeds and comprises adding a toxic quantity of acrolein to the particular body of water.

U.S. Pat. No. 3,250,667, Legator, May 1966 discloses a method of controlling microorganisms encountered in the manufacture of paper. This method employs acrolein to inhibit the formation of slime-forming and corrosion-promoting microorganisms in the aqueous system of a paper-manufacturing plant. Fungi and bacteria are the primary organisms responsible for slimes in paper-making aqueous systems.

U.S. Pat. No. 3,298,906 Knowles, January 1967 discloses the use of acrolein acetals to protect a variety of plants from plant parasitic nematodes. This patent also discloses that the acrolein acetals can be combined with other known fungicides to control a broader spectrum of fungi.

U.S. Pat. No. 3,380,462, Schieber et al., April 1968 discloses a special system to utilize acrolein in a safe manner. This apparatus provides for creating a controlled pressure zone in the liquid to be treated and adding the acrolein to that zone.

U.S. Pat. No. 3,690,857, Blair, Jr., September 1972 discloses the use of acrolein diacetals in watery media to kill aquatic weeds and other undesired life forms. This method will control the growth of these aquatic organisms while avoiding killing the majority of the fish present.

U.S. Pat. No. 4,479,820, Merk et al., October 1984 discloses a process for killing microorganisms or algae in an aqueous system using a water-soluble polycondensation product produced by condensation of acrolein and formaldehyde.

U.S. Pat. No. 4,724,143, Mann et al., February 1988 discloses a synergistic microbiocidal composition comprising a n-alkyldimethylbenzyl ammonium halide or a polycondensation product of acrolein and formaldehyde with a bicyclic polyoxymethyleneoxazolidine. This composition is useful for inhibiting the growth of bacteria in an aqueous system.

PCT International No. WO 88/04671, June 1988 discloses polymers or copolymers of acrolein or of an aldehyde-derivative of acrolein as a biocidal or biostatic composition for microorganisms.

U.S. Pat. No. 4,851,583, Bockowski et al., July 1989 discloses a method for generating acrolein from a precursor that is not hazardous. Acrolein is generated by exposing an acetal of acrolein to suitable non-silica acidic catalytic surfaces. This method allows for in-situ generation of acrolein for the aqueous system to be treated.

As described in an article by G. R. Howell and P. L. Weston-Webb, Jr., "Chesapeake Corp. Finds Acrolein Biocide an Effective Economical Chlorine Substitute", Paper Trade Journal, 160:40-43 (1975) and an article by J. F. Walko and W. L. Smith, Double-Duty Slimicide", Power Engineering, 63:40-41 (1969), these treatment programs were successfully used in a paper mill to replace chlorine as a biological control as well as in cooling water as a slimicide.

"Control of Acid Mine Drainage", Information Circular 9027, U.S. Department of the Interior (1985) discloses the use of sodium lauryl sulfate surfactant to reduce acid production in mines.

DETAILED DESCRIPTION OF THE PREFERRED EMBODIMENT

The present invention pertains to methods for inhibiting the production of acid by *Thiobacillus ferrooxidans* in acid mine waters of mines comprising adding an effective amount for the purpose of acrolein to said acid mine waters thereby controlling the growth of said *Thiobacillus ferrooxidans*.

The acrolein (2-propenal) compound useful in this invention has the formula

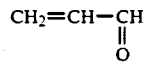

In addition to being a good bactericide, acrolein is also successful from an environmental standpoint. Acrolein is detoxified readily and inexpensively and is environmentally non-persistent. Aqueous solutions of acrolein are readily and conveniently neutralized for disposal with sodium bisulfite. The reaction produces a non-toxic water-soluble salt.

The method of this invention is particularly effective for existing operating mines with acid mine drainage problems. The *Thiobacillus ferrooxidans* bacteria can grow in these mines as they often possess the conditions suitable for the bacteria's growth. As the bacteria thrive, the production of sulfuric acid increases, producing a drainage water of low pH. This acidic water affects the operating and working conditions within the mine to an extent that it must be periodically pumped from the mine to the surface for conventional treatment.

The present inventors have found that when mine drainage is a problem because of its acidity, the addition of a small amount of acrolein will significantly lessen the production of sulfuric acid. The acrolein acts to kill *Thiobacillus ferrooxidans* to reduce the bacteria's production of the sulfuric acid.

This aspect of the invention allows for low level one-time kills that permit non-continuous treatment. This avoids the need for continuous maintenance, and alleviates fear of high acrolein runoff levels. It also avoids the need for unnecessary neutralization treatments.

The acrolein is efficacious because its high vapor pressure quickly allows the chemical to enter the gaseous phase. This permits the acrolein, in dosages as low as 0.1 parts per million, to enter the myriad niches and crevices where the most significant percentage of *Thiobacillus ferrooxidans* is to be found.

The acrolein can be delivered to the mine neat or by any suitable carrier. Water, ether and alcohols can be used as the carrier solvent. An aqueous solution of acrolein in water is the preferred solution, which can be sprayed as an aerosol into the excellent ventilation system of the mine during non-working hours. The acrolein concentration in the mine air should be maintained in excess of 0.5 parts per million (preferred level) for a minimum of eight hours. Maintaining a residual level of acrolein in the mine air is desirable for satisfying both the chemical and biological demand for the acrolein. Biological control is best achieved if a residual level of acrolein is maintained. However, biological control will still be improved as the acrolein demand of the mine is satisfied without a measurable residual.

Upon completion of treatment of the mine, the air can be vented to a scrubber containing a sodium sulfite solution, which will remove residual acrolein and detoxify the material. The mine air can be monitored for its acrolein content by any appropriate analytical method, such as gas chromatography. Once the acrolein is removed, the mine can return to normal operations. Due to the acrolein's ability to kill *Thiobacillus ferrooxidans*, the mine may be relatively free of acid mine drainage until recolonization by *Thiobacillus ferrooxidans* occurs.

Acrolein should also be effective for operating, but out of service mines, and abandoned mines with an acid mine drainage problem, provided that the acrolein can be distributed in the mine water as well as in the air space of the mine. Similarly, acrolein residuals in excess of 0.5 parts per million should be targeted for the mine air space. Mine drainage from the out of service and abandoned mines should be monitored for residual acrolein and detoxified with two moles of sodium sulfite per mole of acrolein (residual) to assure no discharge to the environment.

The treatment dosages are dependent on the severity of the acid production problem and the concentration of the acrolein in the formulated product. Accordingly, a range from about 0.1 parts to about 10 parts acrolein per million parts of mine water should be added. Preferably, acrolein should be added at about 0.1 parts per million to about 0.5 parts per million parts of the mine water to be treated.

The bacterium employed in this study was *Thiobacillus ferrooxidans* ATCC 19859, received from the American Type Culture Collection, Rockville, Md. The strain was originally isolated from mine water.

EXAMPLES

Growth medium flasks were prepared containing 9000 ppm $Fe^{++}$, pH was adjusted below 3.0 with $H_2SO_4$ and acrolein was added to this medium in graded amounts. The flasks were then inoculated with approximately 10% by volume of a fresh three-day-old culture of *Thiobacillus ferrooxidans* into 50 ml of the 9000 ppm $Fe^{++}$ medium in a 125 ml flask stoppered with foam plugs. This inoculated medium was then incubated on a shaker incubator at 28° C.

After 4 days incubation, 5 ml portions of these flasks were transferred to 50 ml of fresh 9000 ppm $Fe^{++}$ medium and then incubated for 3 days. The bactericidal effects of acrolein on *Thiobaccilus ferrooxidans* was observed for acrolein concentrations of 0.5 ppm and higher.

In another experiment, direct addition of the acrolein to the growth medium was performed to determine the growth-inhibiting concentrations of acrolein. Fresh 9000 ppm $Fe^{++}$ medium was sterilized and dispensed in 50 ml volumes in 125 ml sterile flasks plugged with stoppers which allowed gas exchange but preserved sterility (Dispo foam stoppers). Suitable volumes of freshly prepared acrolein stock solutions (50 or 500 ppm) were then prepared. Each flask was then inoculated with 5.0 ml of a three-day old culture of *Thiobacillus ferrooxidans* and placed on a shaker incubator at 28° C.

Observations were made at intervals until growth of the control appeared maximal (3 to 5 days). All growth was compared to the control which received no acrolein. The inhibitory concentrations of acrolein results appear in Table I.

TABLE I

| Acrolein concentration | Growth Observation | |
| --- | --- | --- |
| (ppm) | 3 Days | 5 Days |
| 0.0 | Growth | Growth |
| 0.1 | Growth | Growth |
| 0.2 | No growth | Growth |
| 0.5 | No growth | No growth |
| 1.0 | No growth | No growth |
| 2.0 | No growth | No growth |
| 5.0 | No growth | No growth |
| 10.0 | No growth | No growth |

In a third experiment, the vapor-phase transfer of acrolein to growth medium was evaluated. Fresh 9000 ppm $Fe^{++}$ medium was sterilized and added in 25 ml volumes to sterile 125 ml Warburg flasks with a center well. The center well was not contaminated by the medium. The center wells then received a sufficient volume of a 250 ppm acrolein stock solution to provide a theoretical concentration of acrolein gas in the 125 ml flask volume of 0, 0.1, 0.2, 0.5, 1.0 and 2.0 ppm. The liquid in each well was made up to 1.0 ml with distilled water.

These flasks were then sealed with Dispo stoppers wrapped with parafilm and secured with rubber bands to prevent escape of the acrolein. Two control flasks were included to determine whether sealing the flasks would inhibit growth of the organism. One was sealed as above and the other stoppered with a Dispo plug. The results of this experiment appear in Table II.

TABLE II

| Calculated Acrolein Concentration (ppm) | Growth Response |
| --- | --- |
| 0.0 (open flask) | Growth in 3 days |
| 0.0 (sealed flask) | Growth in 3 days |
| 0.1 | No growth in 7 days |
| 0.2 | No growth in 7 days |
| 0.5 | No growth in 7 days |
| 1.0 | No growth in 7 days |
| 2.0 | No growth in 7 days |

While this invention has been described with respect to particular embodiments thereof, it is apparent that numerous other forms and modifications will be obvious to those skilled in the art. The appended claims generally should be construed to cover all such obvious forms and modifications which are within the true spirit and scope of the present invention.

Having thus described the invention what we claim is:

1. A method for inhibiting the production of acid by *Thiobacillus ferrooxidans* in acid mine waters of mines comprising adding an effective amount for the purpose of acrolein to said acid mine waters thereby controlling the growth of said *Thiobacillus ferrooxidans*.

2. The method as claimed in claim 1 wherein said acrolein is added to said acid mine waters in an amount from about 0.1 parts per million to about 10.0 parts per million parts of said acid mine waters.

3. The method as claimed in claim 2 wherein said acrolein is added to said acid mine waters in an amount from about 0.2 parts per million to about 0.5 parts per million parts of said acid mine waters.

4. The method as claimed in claim 1 wherein the pH of said acid mine waters is about 2.5 to about 4.0.

5. The method as claimed in claim 1 wherein said acid mine waters comprise the acid mine waters of an abandoned mine.

6. The method as claimed in claim 1 wherein said acid mine waters comprise the acid mine waters of an out of service mine.

7. The method as claimed in claim 1 wherein said acid mine waters comprise the acid mine waters of an active mine.

8. The method as claimed in claim 1 wherein said *Thiobacillus ferrooxidans* is growing in the cracks and fissures of said mines.

9. The method as claimed in claim 1 wherein said acrolein is delivered to said mines in the gaseous state.

10. The method as claim in claim 1 wherein said acrolein is delivered to said mines in the liquid state.

11. The method as claimed in claim 1 wherein said acrolein is contained in a water, ether, or alcohol carrier.

12. The method as claimed in claim 1 wherein said mine has sulfur compound, ferrous ion, carbon dioxide, oxygen, and pH less than 5 present.

13. The method as claimed in claim 1 wherein said acid is sulfuric acid.

14. The method as claimed in claim 1 wherein said acid mine waters comprise the mine waters of a coal refuse pile.

15. The method as claimed in claim 1 wherein said acrolein is added intermittently.

* * * * *